United States Patent [19]

Torres-Cardona et al.

[11] Patent Number: 5,523,494

[45] Date of Patent: Jun. 4, 1996

[54] PROCESS FOR THE ISOMERIZATION OF LUTEIN

[75] Inventors: Mario-David Torres-Cardona, San Nicolás de los Garza; Jose Torres-Quiroga, San Pedro Garza García, both of Mexico

[73] Assignee: Industrial Organica, S.A. de C.V., Monterrey, Mexico

[21] Appl. No.: 277,609

[22] Filed: Jul. 20, 1994

[51] Int. Cl.$^6$ ............................ C07C 35/08; C07C 35/18
[52] U.S. Cl. .................. 568/834; 568/816; 568/822; 568/823; 568/824; 568/832
[58] Field of Search ..................... 568/816, 834, 568/822, 828, 823, 824, 832

[56] References Cited

U.S. PATENT DOCUMENTS

| | | | |
|---|---|---|---|
| 3,523,136 | 8/1970 | Grant et al. | 260/617 |
| 3,523,138 | 8/1970 | Grant | 568/816 |
| 3,535,426 | 10/1970 | Hawks | 424/343 |
| 3,539,686 | 11/1970 | Rosenberg | 424/195 |
| 3,558,712 | 1/1971 | Surmatis | 568/816 |
| 3,783,099 | 1/1974 | Matoushek | 195/2 |
| 3,989,757 | 11/1976 | Surmatis | 568/816 |
| 5,382,714 | 1/1995 | Khachik | 568/834 |

FOREIGN PATENT DOCUMENTS

| | | |
|---|---|---|
| 2535963 | 3/1975 | Germany. |
| 1150827 | 5/1969 | United Kingdom. |

OTHER PUBLICATIONS

Sander et al., Anal. Chem., 1994, 66, 1667–1674.
Ittah et al., J. Agric. Food Chem., 1993, 41, 889–901.
Gau et al., J. of Chromatography, 262(1983), 277–284.
Fletcher, Poultry Science, 1992, 71, 733–743.
Andrewes, Acta Chem. Scand. B28 (1974) No. 1.
AOAC Official Methods of Analysis, "Carotenr and Xantophylls in Dried Plant Material and Mixed Feeds Spectrophotometic Method" 1984, 835–836.
Quackenbush et al., J. of the A.O.A.C., 55, 617(1972).
Karrer et al., Helvetica Chimica Acta, vol. 30, 266–267 (1947).

*Primary Examiner*—Werren B. Lone
*Attorney, Agent, or Firm*—Abelman, Frayne & Schwab

[57] ABSTRACT

A process to obtain a product with a high *zeaxanthin* content, to be used mainly as an ingredient in poultry feed to enhance the pigmentation of broiler chickens and egg yolk, by reacting at a controlled temperature and pressure, marigold (Tagetes erecta L.) meal or its oleoresin, or formulations containing lutein, with strongly alkaline aqueous solutions under controlled conditions, to isomerize the luteine into *zeaxanthin* in a product with a higher pigmenting activity.

30 Claims, No Drawings

PROCESS FOR THE ISOMERIZATION OF LUTEIN

BACKGROUND OF THE INVENTION

An adequate pigmentation is a major concern of the poultry industry. Not only it is synonymous of good healthy birds, but at the same time it is also an important marketing strategy in many cultures. Very frequently, poultry producers make considerable efforts in order to obtain an attractively pigmented bird-carcass that appeals to the eye of the consumer.

To satisfy the market preferences, chicken producers have traditionally supplemented the poultry diets with carotenoid (particularly hydroxicarotenoids or xanthophylls) containing extracts or meals of plant origin that are responsible for the desired yellow-orange color in the broiler chickens and in egg yolks. A widely used source of xanthophylls is marigold meal and its extract. The carotenoids from marigold contain approximately from 85 to 90% of lutein ($\beta,\epsilon$-caroten-3,3'-diol) and from 2 to 4% of *zeaxanthin* ($\beta,\beta$-caroten 3,3'-diol) (F. W. Quackenbush, 1972. J.AOAC, 55 (3), 617–21). These hydroxicarotenoids occur in the plant as esters of fatty acids, mainly palmitic, myristic and stearic (W. Gau. 1983, J. Chromatogr. 262, 277–84).

However, it has been proved that a more efficient pigmentation is obtained when the xanthophylls are in their free form (Fletcher, D. L. 1986, Poult. Sci., 65(9), 1708–14) after the ester link has been broken by means of a saponification process. As a matter of fact, most of the pigment producers carry on a saponification process in order to improve the bioavailability of the xanthophylls.

Furthermore, it has been demonstrated that a synergistic effect occurs when carotenoids like lutein and *zeaxanthin* are mixed with other natural or synthetic pigments for broiler chicken and egg yolk pigmentation (U.S. Pat. No. 3,539,686 of Nov. 10, 1970 to Ralph Rosenberg).

Different methods have been practiced in the past decades for the preparation of xanthophyll concentrates from marigold meal. As an example, in the U.S. Pat. No. 3,523,138 from Aug. 4, 1970. issued to Eastman Kodak Co., a process is described wherein the marigold meal is reacted with an alcoholic alkali solution. After saponification the mixture is diluted with water and the xanthophylls are separated by solvent extraction by means of water insoluble solvent like isopropyl ether.

U.S. Pat. No. 3,535,426 dated October 1970, issued also to Eastman Kodak Co., describes a method to stabilize xanthophylls by adding an antioxidant ethoxyquin (6.ethoxy-2,2,4-trimethil-1,2-hydroquinoline) and fat, and heating the mixture afterwards. The product obtained is very stable and does not degrade appreciably.

Also Ger. Offen. 2,535,963 dated Mar. 4, 1976, issued to CPC International Inc., describes a process to stabilize xanthophylls by partial saponification using a solution of potassium hydroxide in methanol.

U.S. Pat. No. 3,783,099 dated >Jan. 1st 1974 issued to Ralston Purina Co., a process is described where an enzymatic hydrolysis of the cellulosic material of tho marigold meal, improves the extraction of the xanthophylls with a non polar solvent.

Recently some fermentative processes have been described wherein the reproduction of improved strains of Flavobacterium Multivorum result in the obtainment of *zeaxanthin* extracts with a pigment activity 2 to 3 times higher than that of marigold extracts, and are suggested as an alternative to naturally occurring carotenoids; as described on PCT Int. Appln. WO 91 03,571 dated Mar. 21, 1991, issued to Applied Biotechnology, Inc.

Traditional sources of *zeaxanthin* have been the extracts and meals of yellow corn and yellow corn gluten.

Years ago, *Karrer and Jucker* in 1947 (Helv. Chim. Acta. 30,266–7) obtained *zeaxanthin* by isomerizing lutein in a reaction catalyzed with sodium ethoxide in the presence of ethanol and benzene. A. G. Andrews, also in 1947 (Acta Chem. Scand. B 28 No. 1) obtained *zeaxanthin* from lutein using potassium methoxide in the presence of methanol and dimethylsulfoxide. In both procedures a poor yield was obtained resulting in a great loss of pigment. The economy of such processes is inadequate for industrial purposes. However, they demonstrated the feasibility to isomerize lutein into *zeaxanthin*.

In other words, isomerization of lutein into *zeaxanthin* has been carried out in academic research basis in a catalytic organic phase in the presence of solvents with a very strong alcoholic alkaline solutions which could cause a very violent exothermic reaction in the presence of water or humidity.

This process is related with the isomerization of lutein into *zeaxanthin* in a non catalytic aqueous phaso which does not needs the presence of solvents.

In the marigolds meal extracts available in the market, *zeaxanthin* represents only from 4 to 6% of the total xanthophill content. Since the pigment activity of this carotenoid is higher than that of lutein, applicants have developed a process where a higher. concentration of *zeaxanthin* is obtained, and hence the pigment efficiency of the extract containing this carotenoid is improved.

SUMMARY OF THE INVENTION

It is therefore a main object of the present invention, to provide a process to isomerize lutein into *zeaxanthin* in a non catalytic aqueous phase with strongly alkaline aqueous solutions and under controlled conditions which does not need the presence of solvents.

It is also a main object of the invention, to provide a process to isomerize lutein into *zeaxanthin* from marigold (Tagetes erecta L.) meal, its oleoresin or formulations containing lutein.

It is still a main object of the invention, to provide a process to isomerize lutein into *zeaxanthin* to produce a product with a high *zeaxanthin* content which can be used to pigment broiler chickens and egg yolks, as a pigmenting ingredient in aquaculture and as an ingredient for food consumption.

It is a further main object of the present invention, to provide a process to isomerize lutein into *zeaxanthin*, of the above disclosed nature, wherein the presence of the *zeaxanthin* in the obtained product represents from 5 to 50% of the total xanthophylls, usually from 8 to 30%, and preferably from 10 to 20%.

It is an additional object of the present invention, to provide a process to isomerize lutein into *zeaxanthin*, of the above disclosed nature, which is safe, and commercially and economically viable because it is carried out in a non catalytic aqueous phase which consequently does not require organic solvents.

These and other objects and advantages of the present invention will be apparent to persons skilled in the art, from the following description of the specific embodiments of the invention, represented by the examples.

DETAILED DESCRIPTION OF THE INVENTION

The standard method of analysis accepted in the industry to quantify total xanthophylls in marigold meals and its extracts is described in the "AOAC Official Method of Analysis" (edited by Sidney Williams, Fourteenth edition, pages 835-6, 1984).

The HPLC methods to separate, identify and quantify lutein and zeaxanthin are described in the work of Yitzhak Itta (J. Agric. Food. Chem., 1993, 41, 899–901) and of Lane C. Sander (Anal. Chem., 1994, 66, 1667–1674).

The process occurs according to the following mechanism:

LUTEIN

[chemical structure of lutein with arrows showing H removal]

$B^-/H_2O$, $\Delta$

ZEAXANTHIN

[chemical structure of zeaxanthin]

$R =$ [polyene chain structure]
$B^- =$ BASE

The extract that contains the lutein can be maintained at any temperature from 25° to 180° C., preferably from 70° to 110° C. The slow addition of strongly alkaline aqueous solution is followed, wherein the alkali can be sodium hydroxide (NaOH), potassium hydroxide (KOH), calcium hydroxide ($Ca(OH)_2$), sodium carbonate ($Na_2CO_3$), ammonium hydroxide ($NH_4OH$), or any other similar compound, or their mixtures. Organic basis like ethylamine, ethanolamine, morpholine or others of a similar nature, or their mixtures can also be used.

The alkali concentration in the aqueous solution can be from 5 to 50% by weight, preferably between 25% and 45% by weight. The amount of alkali can be in the range of 0.1 to 1.0 parts for one part of marigold meal extract, or more preferably from 0.3 to 0.7 parts of alkali to one part of the lutein containing concentrate.

The reaction time is strongly dependent on the temperature and amount of alkali used, but can be from 5 to 96 hours, usually from 16 to 36 hours, and preferably from 30 to 48 hours..

The process can be carried out in a reactor or container at atmospheric pressure, but if shorter reaction times are desired the pressure can be increased from 5 to 150 psig, preferably from 20 to 50 psig. By this means the reaction time can be from 5 minutes to 12 hours, usually from 3 to 8 hours. It is desired to employ an inert atmosphere using either steam, nitrogen, carbon dioxide or similar compounds or their mixtures. If desired, the reaction can be carried out at a reduced pressure to avoid xanthophyll degradation.

Typical examples are illustrated on Table 1, indicating some of the results that have been obtained. These are examples only, and should not be interpreted as limiting the scope of this invention.

TABLE 1

| Lot No. | 1 | 2 | 3 | 4 |
|---|---|---|---|---|
| Alkali | KOH | NaOH | $Na_2CO_3$ | KOH |
| Alkali/Extract, w/w | 0.3 | 1.0 | 0.5 | 0.5 |
| Temperature °C. | 80 | 90 | 105 | 95 |
| Pressure, atm. | 0.5 | 1.0 | 2.0 | 1.0 |
| Time, Hr. | 48 | 30 | 3 | 36 |
| [1]Initial Lutein % | 85.5 | 85.5 | 85.5 | 85.5 |
| Final lutein % | 68.9 | 66.2 | 60.8 | 68.3 |
| [2]Initial Zeaxanthin % | 4.5 | 4.5 | 4.5 | 4.5 |
| Final zeaxanthin % | 16.1 | 18.7 | 24.0 | 15.8 |

[1,2]: the initial extract contents 97 grams of total xanthophylls per kilo of extract, and on this value are calculated the percentages.

①, ②: the initial extract contents 97 grams of total xanthophylls per kilo of extract, and on this value are calculated the percentages.

The product obtained can be formulated as a water dispersion by means of suitable emulsifiers or can be dispersed on a carrier to make a premix or can be further concentrated by solvent extraction.

What we claim is:

1. A process to isomerize lutein into zeaxanthin, comprising treating a lutein reaction substrate selected from the group consisting of marigold flowers, marigold leaves, marigold meal, marigold oleoresin, or mixtures, extracts, or concentrates thereof, yellow corn and yellow corn gluten, or mixtures, extracts or concentrates thereof, with a strongly aqueous alkaline solution under controlled conditions of temperature and pressure for a length of time that depends on the degree of the desired isomerization.

2. The process according to claim 1, in which the lutein substrate is in a hydrolyzed or esterified form.

3. The process according to claim 1, in which the lutein reaction substrate is an extract or concentrate obtained from the group consisting of marigold flowers (Tagetes erecta L.) or marigold meal.

4. The process according to claim 1, in which the lutein reaction substrate contains xanthophylls, comprising mainly free lutein in any proportion.

5. The process according to claim 1, wherein the lutein reaction substrate contains xanthophylls, comprising mainly lutein in a naturally occurring esterified form, in any proportion.

6. The process according to claim 1 in which the aqueous alkali solutions are aqueous solutions which contain from about 5 to about 50%, by weight, of alkali.

7. The process according to claim 1, in which the alkali solutions are selected from the group consisting of alkali saturated or oversaturated solutions.

8. The process according to claim 1 in which the alkali is selected from the group consisting of potassium hydroxide, sodium hydroxide, sodium carbonate, ammonium hydroxide, ammonia, or their mixtures, or in its anhydrous form.

9. The process according to claim 1 in which the alkali is an organic base selected from the group consisting of ethanolamine, ethylamine, morpholine, or mixtures thereof.

10. The process according to claim 1, in which the ratio, by weight, of alkali to the lutein containing substrate, is about 0.05:5.

11. The process according to claim 1, in which the reaction time of the alkaline solution and the lutein containing substrate is from about 5 minutes to about 96 hours.

12. The process according to claim 1, in which the reaction is catalyzed by enzymatjc means, like a catalase or an isomerase.

13. The process according to claim 1, in which the isomerization of lutein is carried out at pressures selected from the group consisting of from about 5 to about 150 psig, and atmospheric pressure.

14. The process according to claim 1 in which the isomerization reaction is carried out at a reduced pressure.

15. A process according to claim 1, in which the reaction is carried out under an inert atmosphere of carbon dioxide, nitrogen, or their mixtures.

16. The process according to claim 1, in which the reaction temperature is from about 25° to 180° C.

17. The process according to claim 1, in which the isomerization reaction time is improved by means of ultrasonic waves.

18. The process according to claim 1, in which, in the product obtained, the *zeaxanthin* represents from about 5 to about 50% of the total xanthophylls.

19. The process according to claim 1, in which the product obtained or its formulations, can be used to pigment broiler chickens and egg yolks.

20. The process according to claim 1, in which the product obtained or its formulations, can be used as pigmenting ingredient in aquaculture.

21. The process according to claim 1, in which the product obtained or its formulations, can be used as an ingredient for food consumption.

22. A lutein isomerized substrate having a *zeaxanthin* content from about 5 % to about 50% of the total xanthophylls, produced by isomerizing a lutein reaction substrate selected from the group consisting of marigold flowers, marigold leaves, marigold meal, marigold oleoresin, or mixtures, extracts, or concentrates thereof, yellow corn and yellow corn gluten, or mixtures, extracts, or concentrates thereof, with a strongly aqueous alkaline solution under controlled conditions of temperature and pressure for a length of time that depends on the degree of the desired isomerization.

23. The process according to claim 1, in which the lutein reaction substrate is any natural material containing xanthophylls selected from the group consisting of yellow corn, yellow corn gluten, or its extracts or mixtures.

24. The process according to claim 1, in which the ratio, by weight, of alkali to the lutein containing substrate is about 0.1:3.

25. The process according to claim 1, in which the ratio, by weight, of alkali to the lutein containing substrate is about 0.2:1.

26. The process according to claim 16, in which the reaction temperature is from about 70° C. to about 110° C.

27. The process according to claim 1, in which in the product obtained the *zeaxanthin* represents from about 8% to about 30% of the total xanthophylls.

28. The process according to claim 1, in which in the product obtained the *zeaxanthin* represents from about 10% to about 20% of the total xanthophylls.

29. A lutein isomerized substrate according to claim 22, having a *zeaxanthin* content of from about 8% to about 30% of the total xanthophylls.

30. A lutein isomerized substrate according to claim 22, having a *zeaxanthin* content of from about 10% to about 20% of the total xanthophylls.

\* \* \* \* \*